(12) United States Patent
Yokoyama et al.

(10) Patent No.: US 8,178,301 B2
(45) Date of Patent: May 15, 2012

(54) MUTANT SEPRS, AND METHOD FOR SITE-SPECIFIC INTRODUCTION OF PHOSPHOSERINE INTO PROTEIN USING THE SAME

(75) Inventors: Shigeyuki Yokoyama, Kanagawa (JP); Ryuya Fukunaga, Tokyo (JP); Shun-ichi Sekine, Tokyo (JP)

(73) Assignee: Riken, Wako-shi, Saitama (JP)

( * ) Notice: Subject to any disclaimer, the term of this patent is extended or adjusted under 35 U.S.C. 154(b) by 340 days.

(21) Appl. No.: 12/318,344

(22) Filed: Dec. 24, 2008

(65) Prior Publication Data

US 2009/0233290 A1    Sep. 17, 2009

Related U.S. Application Data

(63) Continuation of application No. PCT/JP2007/063414, filed on Jun. 28, 2007.

(30) Foreign Application Priority Data

Jun. 28, 2006 (JP) ................................. 2006-178642

(51) Int. Cl.
*C12Q 1/68* (2006.01)
*C12N 9/00* (2006.01)
*C12N 15/63* (2006.01)
*C12N 1/21* (2006.01)

(52) U.S. Cl. .................... 435/6.13; 435/183; 435/252.3; 435/320.1; 536/23.2

(58) Field of Classification Search ........................ None
See application file for complete search history.

(56) References Cited

U.S. PATENT DOCUMENTS 7,723,069 B2 * 5/2010 Soll et al. ..................... 435/69.1

OTHER PUBLICATIONS

EP Search Report dated May 31, 2010 for Application No. 07768165.8.
Fukunaga, R. et al., "Biochemical and Biophysical Research Communications," Biochem. and Biophys. Res. Comm., vol. 372, pp. 480-485 (2008).
Perich, J. W., et al., "Efficient solution-phase synthesis of multiple O-phosphoseryl-containing peptides related to casein and statherin," Intl. J. Peptide Protein Res., vol. 40, No. 2, pp. 81-88 (1992).
Wang, L., et al., "Expanding the Genetic Code," Annu. Rev. Biophys. Biomol. Struct., vol. 35, pp. 225-249 (2006).

* cited by examiner

*Primary Examiner* — Kagnew H Gebreyesus
(74) *Attorney, Agent, or Firm* — Birch, Stewart, Kolasch & Birch, LLP

(57) ABSTRACT

A mutant SepRS which is suitable for a site-specific introduction of phosphoserine into a protein is prepared by analyzing the structure and functions of a phosphoseryl-tRNA synthetase (SepRS) derived from an archaebacterium. A mutant SepRS composed of an amino acid sequence depicted in SEQ ID NO:2, in which any one or more of glutamic acids at position-418 and position-420 and threonine at position-423 are substituted with other amino acid, and having enhanced binding affinity with a suppressor tRNA as compared with a wild type phosphoseryl-tRNA synthetase (SepRS) composed of an amino acid sequence depicted in SEQ ID NO:2 is provided.

13 Claims, 9 Drawing Sheets

(9 of 9 Drawing Sheet(s) Filed in Color)

FIG. 2
(a)
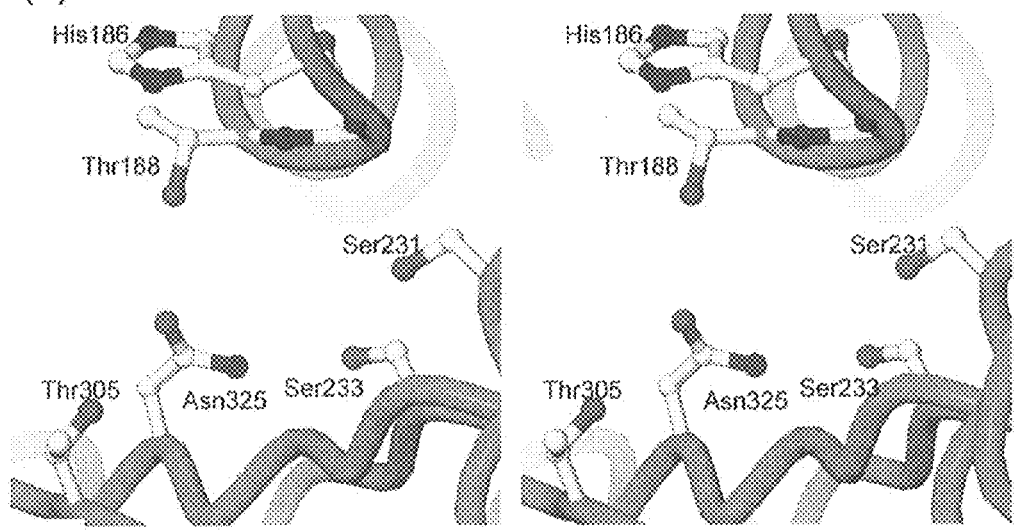
(b)
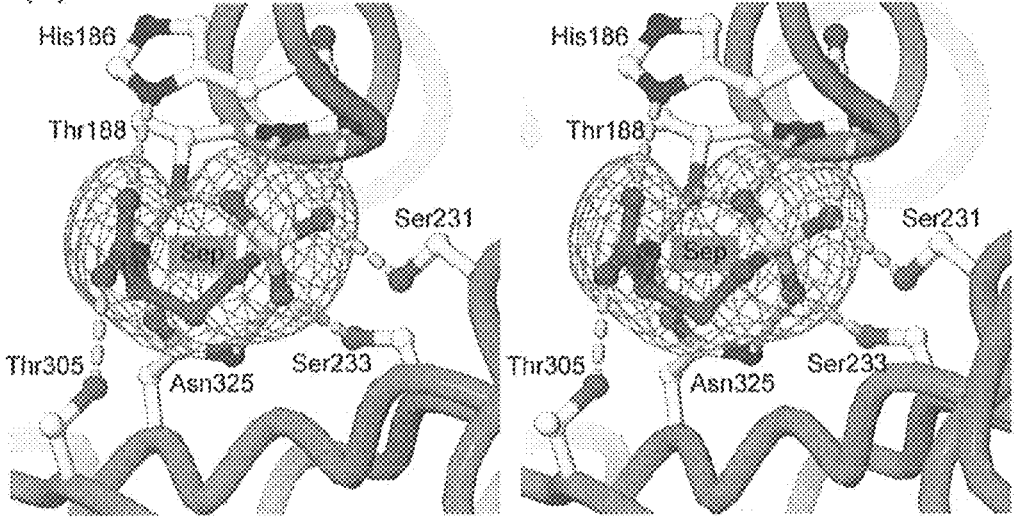

FIG. 4
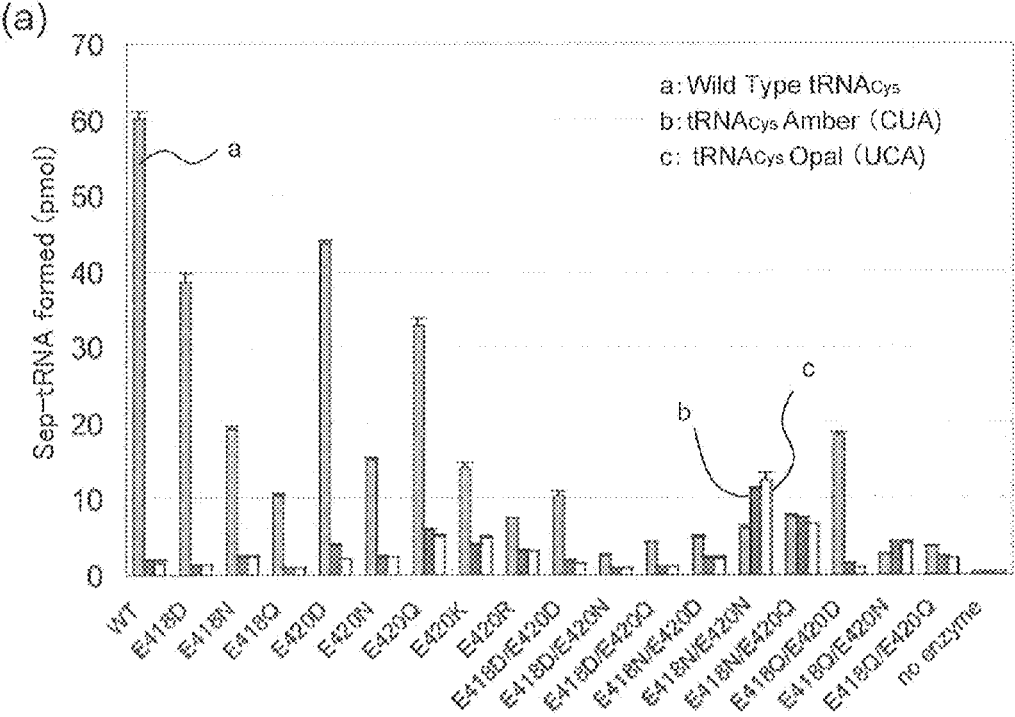
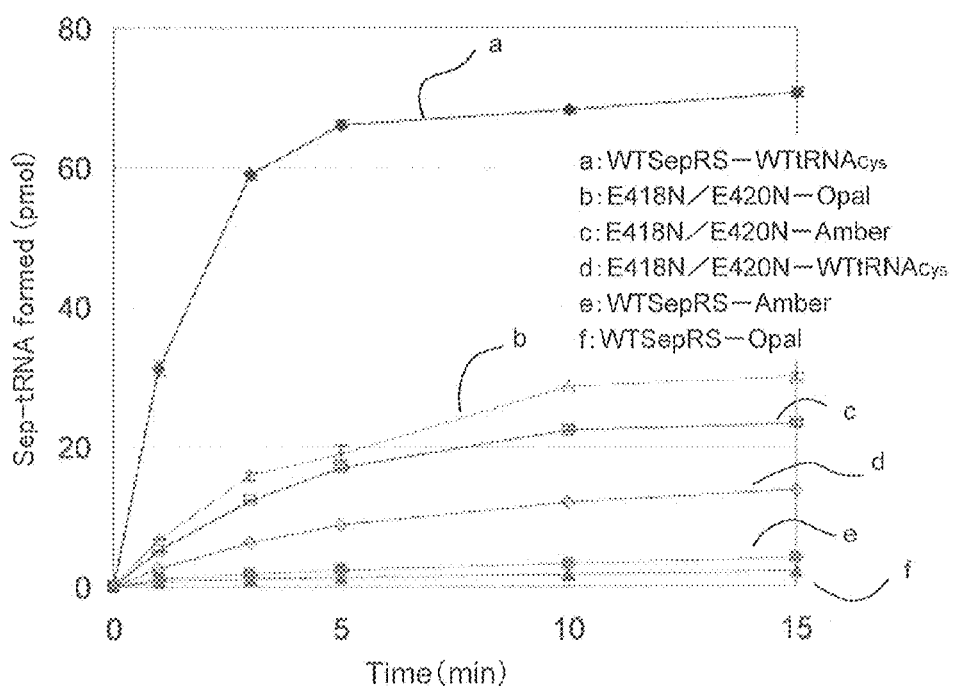

SEQUENCE LISTING

```
<160> NUMBER OF SEQ ID NOS: 3

<210> SEQ ID NO 1
<211> LENGTH: 1605
<212> TYPE: DNA
<213> ORGANISM: Archaeoglobus fulgidus
<220> FEATURE:
<221> NAME/KEY: CDS
<222> LOCATION: (1)..(1605)
<223> OTHER INFORMATION:

<400> SEQUENCE: 1 atg aaa ttc gac cct cag aag tac aga gag ctt gca gag aag gac ttc      48
```

```
            Met Lys Phe Asp Pro Gln Lys Tyr Arg Glu Leu Ala Glu Lys Asp Phe
            1               5                   10                  15 gaa gct gca tgg aag gcc gga aag gaa att ctg gct gag aga agt ccg        96
Glu Ala Ala Trp Lys Ala Gly Lys Glu Ile Leu Ala Glu Arg Ser Pro
                20                  25                  30 aac gag ctt tat ccc aga gtg ggt ttc agc ttt ggt aag gag cac cct       144
Asn Glu Leu Tyr Pro Arg Val Gly Phe Ser Phe Gly Lys Glu His Pro
            35                  40                  45 cta ttt gcc aca att cag aga ttg agg gag gct tac ctc tcc ata gga       192
Leu Phe Ala Thr Ile Gln Arg Leu Arg Glu Ala Tyr Leu Ser Ile Gly
        50                  55                  60 ttt tct gag gtt gtg aat ccg ctg att gtt gag gat gtc cac gtt aaa       240
Phe Ser Glu Val Val Asn Pro Leu Ile Val Glu Asp Val His Val Lys
65                  70                  75                  80 aag cag ttc gga agg gag gct ttg gcc gtc ctc gac agg tgc ttc tac       288
Lys Gln Phe Gly Arg Glu Ala Leu Ala Val Leu Asp Arg Cys Phe Tyr
                85                  90                  95 ctt gcc aca ctc ccc aag ccc aat gtg ggt atc tct gcg gag aaa atc       336
Leu Ala Thr Leu Pro Lys Pro Asn Val Gly Ile Ser Ala Glu Lys Ile
            100                 105                 110 agg cag att gag gcc ata aca aag agg gag gtt gat tca aag ccc ctg       384
Arg Gln Ile Glu Ala Ile Thr Lys Arg Glu Val Asp Ser Lys Pro Leu
        115                 120                 125 cag gag att ttc cac cgc tac aag aag ggt gag att gac gga gac gat       432
Gln Glu Ile Phe His Arg Tyr Lys Lys Gly Glu Ile Asp Gly Asp Asp
    130                 135                 140 ttg agc tac ctt att gct gaa gtt ctg gac gtt gat gac ata act gct       480
Leu Ser Tyr Leu Ile Ala Glu Val Leu Asp Val Asp Asp Ile Thr Ala
145                 150                 155                 160 gta aag ata ctc gat gaa gtc ttt cca gag ttc aag gag cta aag cca       528
Val Lys Ile Leu Asp Glu Val Phe Pro Glu Phe Lys Glu Leu Lys Pro
                165                 170                 175 atc tcc agc acg ctc act ctc aga agc cac atg acg act ggc tgg ttc       576
Ile Ser Ser Thr Leu Thr Leu Arg Ser His Met Thr Thr Gly Trp Phe
            180                 185                 190 ata act ttg agc cac atc gcc gac aag ctc ccc cta ccc atc aaa ctc       624
Ile Thr Leu Ser His Ile Ala Asp Lys Leu Pro Leu Pro Ile Lys Leu
        195                 200                 205 ttc agc atc gac cgc tgc ttc agg agg gag cag gga gag gat gcg acg       672
Phe Ser Ile Asp Arg Cys Phe Arg Arg Glu Gln Gly Glu Asp Ala Thr
    210                 215                 220 agg ctt tac acc tac ttc tca gcc agc tgt gtt ctg gtt gat gaa gag       720
Arg Leu Tyr Thr Tyr Phe Ser Ala Ser Cys Val Leu Val Asp Glu Glu
225                 230                 235                 240 ctc agc gtt gat gac gga aag gct gtt gcc gag gct ctg cta agg cag       768
Leu Ser Val Asp Asp Gly Lys Ala Val Ala Glu Ala Leu Leu Arg Gln
                245                 250                 255 ttc ggc ttc gag aac ttc agg ttc agg aag gac gag aag agg agc aag       816
Phe Gly Phe Glu Asn Phe Arg Phe Arg Lys Asp Glu Lys Arg Ser Lys
            260                 265                 270 tac tac atc ccc gac acg cag aca gag gta ttt gcc ttc cat ccg aag       864
Tyr Tyr Ile Pro Asp Thr Gln Thr Glu Val Phe Ala Phe His Pro Lys
        275                 280                 285 ctc gtt ggc tca agt aca aag tac agc gac ggc tgg att gag att gcc       912
Leu Val Gly Ser Ser Thr Lys Tyr Ser Asp Gly Trp Ile Glu Ile Ala
    290                 295                 300 acc ttc ggc atc tac tct ccc acg gcc ctt gcg gag tac gac att ccc       960
Thr Phe Gly Ile Tyr Ser Pro Thr Ala Leu Ala Glu Tyr Asp Ile Pro
305                 310                 315                 320 tat ccc gtg atg aat ctc ggc tta gga gtg gaa agg ctg gca atg att      1008
```

|     |     |     |     |     |     |     |     |     |     |     |     |     |     |     |     |
|---|---|---|---|---|---|---|---|---|---|---|---|---|---|---|---|
| Tyr | Pro | Val | Met | Asn | Leu | Gly | Leu | Gly | Val | Glu | Arg | Leu | Ala | Met | Ile |
|     |     |     |     | 325 |     |     |     | 330 |     |     |     |     | 335 |     |     |

```
ctc tat ggc tac gac gat gtg agg aag atg gtt tac ccg cag att cat    1056
Leu Tyr Gly Tyr Asp Asp Val Arg Lys Met Val Tyr Pro Gln Ile His
            340                 345                 350 gga gag att aag cta agc gac ctc gac att gcg agg gaa ata aag gtt    1104
Gly Glu Ile Lys Leu Ser Asp Leu Asp Ile Ala Arg Glu Ile Lys Val
        355                 360                 365 aag gag gtc ccc cag act gct gta ggg ctg aaa att gcc cag agc att    1152
Lys Glu Val Pro Gln Thr Ala Val Gly Leu Lys Ile Ala Gln Ser Ile
    370                 375                 380 gtg gag acg gca gaa aag cac gct tcg gag ccg agc ccc tgc agc ttt    1200
Val Glu Thr Ala Glu Lys His Ala Ser Glu Pro Ser Pro Cys Ser Phe
385                 390                 395                 400 ttg gca ttt gaa ggg gag atg atg ggc aga aat gtg agg gtt tac gtg    1248
Leu Ala Phe Glu Gly Glu Met Met Gly Arg Asn Val Arg Val Tyr Val
                405                 410                 415 gtt gag gag gag gag aac acg aag cta tgc ggt cct gct tac gcc aac    1296
Val Glu Glu Glu Glu Asn Thr Lys Leu Cys Gly Pro Ala Tyr Ala Asn
            420                 425                 430 gag gtt gtt gtt tac aaa ggg gac atc tac ggc att cca aaa acc aag    1344
Glu Val Val Val Tyr Lys Gly Asp Ile Tyr Gly Ile Pro Lys Thr Lys
        435                 440                 445 aag tgg agg agc ttc ttt gag gag ggt gtg cct acc ggc att agg tac    1392
Lys Trp Arg Ser Phe Phe Glu Glu Gly Val Pro Thr Gly Ile Arg Tyr
    450                 455                 460 atc gac ggc ttt gcc tac tat gca gca agg aag gtt gag gag gct gcg    1440
Ile Asp Gly Phe Ala Tyr Tyr Ala Ala Arg Lys Val Glu Glu Ala Ala
465                 470                 475                 480 atg agg gaa cag gag gag gtg aag gtg aaa gct agg att gta gag aac    1488
Met Arg Glu Gln Glu Glu Val Lys Val Lys Ala Arg Ile Val Glu Asn
                485                 490                 495 ctc tcg gac ata aac ctt tac atc cac gaa aac gtc agg agg tac att    1536
Leu Ser Asp Ile Asn Leu Tyr Ile His Glu Asn Val Arg Arg Tyr Ile
            500                 505                 510 ctc tgg aag aag ggg aag ata gac gtc aga gga cca ctg ttc gtt acc    1584
Leu Trp Lys Lys Gly Lys Ile Asp Val Arg Gly Pro Leu Phe Val Thr
        515                 520                 525 gtt aag gcc gaa att gag tag                                        1605
Val Lys Ala Glu Ile Glu
    530

<210> SEQ ID NO 2
<211> LENGTH: 534
<212> TYPE: PRT
<213> ORGANISM: Archaeoglobus fulgidus

<400> SEQUENCE: 2

Met Lys Phe Asp Pro Gln Lys Tyr Arg Glu Leu Ala Glu Lys Asp Phe
1               5                   10                  15

Glu Ala Ala Trp Lys Ala Gly Lys Glu Ile Leu Ala Glu Arg Ser Pro
                20                  25                  30

Asn Glu Leu Tyr Pro Arg Val Gly Phe Ser Phe Gly Lys Glu His Pro
            35                  40                  45

Leu Phe Ala Thr Ile Gln Arg Leu Arg Glu Ala Tyr Leu Ser Ile Gly
        50                  55                  60

Phe Ser Glu Val Val Asn Pro Leu Ile Val Glu Asp Val His Val Lys
65                  70                  75                  80

Lys Gln Phe Gly Arg Glu Ala Leu Ala Val Leu Asp Arg Cys Phe Tyr
                85                  90                  95
```

```
Leu Ala Thr Leu Pro Lys Pro Asn Val Gly Ile Ser Ala Glu Lys Ile
            100                 105                 110

Arg Gln Ile Glu Ala Ile Thr Lys Arg Glu Val Asp Ser Lys Pro Leu
            115                 120                 125

Gln Glu Ile Phe His Arg Tyr Lys Lys Gly Ile Asp Gly Asp
130                 135                 140

Leu Ser Tyr Leu Ile Ala Glu Val Leu Asp Val Asp Asp Ile Thr Ala
145                 150                 155                 160

Val Lys Ile Leu Asp Glu Val Phe Pro Glu Phe Lys Glu Leu Lys Pro
                165                 170                 175

Ile Ser Ser Thr Leu Thr Leu Arg Ser His Met Thr Thr Gly Trp Phe
                180                 185                 190

Ile Thr Leu Ser His Ile Ala Asp Lys Leu Pro Leu Pro Ile Lys Leu
                195                 200                 205

Phe Ser Ile Asp Arg Cys Phe Arg Arg Glu Gln Gly Glu Asp Ala Thr
                210                 215                 220

Arg Leu Tyr Thr Tyr Phe Ser Ala Ser Cys Val Leu Val Asp Glu Glu
225                 230                 235                 240

Leu Ser Val Asp Asp Gly Lys Ala Val Ala Glu Ala Leu Leu Arg Gln
                245                 250                 255

Phe Gly Phe Glu Asn Phe Arg Phe Arg Lys Asp Glu Lys Arg Ser Lys
                260                 265                 270

Tyr Tyr Ile Pro Asp Thr Gln Thr Glu Val Phe Ala Phe His Pro Lys
                275                 280                 285

Leu Val Gly Ser Ser Thr Lys Tyr Ser Asp Gly Trp Ile Glu Ile Ala
                290                 295                 300

Thr Phe Gly Ile Tyr Ser Pro Thr Ala Leu Ala Glu Tyr Asp Ile Pro
305                 310                 315                 320

Tyr Pro Val Met Asn Leu Gly Leu Gly Val Glu Arg Leu Ala Met Ile
                325                 330                 335

Leu Tyr Gly Tyr Asp Asp Val Arg Lys Met Val Tyr Pro Gln Ile His
                340                 345                 350

Gly Glu Ile Lys Leu Ser Asp Leu Asp Ile Ala Arg Glu Ile Lys Val
                355                 360                 365

Lys Glu Val Pro Gln Thr Ala Val Gly Leu Lys Ile Ala Gln Ser Ile
                370                 375                 380

Val Glu Thr Ala Glu Lys His Ala Ser Glu Pro Ser Pro Cys Ser Phe
385                 390                 395                 400

Leu Ala Phe Glu Gly Glu Met Met Gly Arg Asn Val Arg Val Tyr Val
                405                 410                 415

Val Glu Glu Glu Asn Thr Lys Leu Cys Gly Pro Ala Tyr Ala Asn
                420                 425                 430

Glu Val Val Tyr Lys Gly Asp Ile Tyr Gly Ile Pro Lys Thr Lys
                435                 440                 445

Lys Trp Arg Ser Phe Phe Glu Glu Gly Val Pro Thr Gly Ile Arg Tyr
                450                 455                 460

Ile Asp Gly Phe Ala Tyr Tyr Ala Ala Arg Lys Val Glu Glu Ala Ala
465                 470                 475                 480

Met Arg Glu Gln Glu Glu Val Lys Val Lys Ala Arg Ile Val Glu Asn
                485                 490                 495

Leu Ser Asp Ile Asn Leu Tyr Ile His Glu Asn Val Arg Arg Tyr Ile
                500                 505                 510

Leu Trp Lys Lys Gly Lys Ile Asp Val Arg Gly Pro Leu Phe Val Thr
```

```
                        515                 520                 525
Val Lys Ala Glu Ile Glu
    530

<210> SEQ ID NO 3
<211> LENGTH: 72
<212> TYPE: DNA
<213> ORGANISM: Archaeoglobus fulgidus

<400> SEQUENCE: 3
gccagggtgg cagaggggct atgcggcgga ctgcagatcc gctttacccc ggttcgaatc    60
cgggccctgg ct                                                       72
```

US 8,178,301 B2

MUTANT SEPRS, AND METHOD FOR SITE-SPECIFIC INTRODUCTION OF PHOSPHOSERINE INTO PROTEIN USING THE SAME

RELATED APPLICATIONS

This application is a Continuation Application of International Application PCT/JP2007/063414, filed in the Japanese Patent Office on Jun. 28, 2007. This application is based upon and claims the benefit of priority from Japanese Patent Application No. 2006-178642, filed Jun. 28, 2006, the entire contents of which are incorporated herein by reference.

TECHNICAL FIELD

The present invention relates to a mutant phosphoseryl-tRNA synthetase (SepRS), a method for the production of a protein having phosphoserine integrated thereinto through site-specific introduction of phosphoserine into a protein by using the subject synthetase, and a vector and a kit therefor, and so on.

BACKGROUND ART

Proteins having a non-naturally occurring amino acid integrated thereinto (hereinafter referred to as "alloproteins"), in which an amino acid residue at a desired location in a protein is substituted with an amino acid other than 20 kinds of amino acids normally involved in protein synthesis (non-naturally occurring amino acids), offer effective means for the functional or structural analysis of proteins. For example, proteins containing a non-naturally occurring amino acid are used for intramolecular labeling, crosslinking of proteins and structural analysis by X-ray or NMR (see, for example, Non-Patent Document 1) and analysis of a signal transduction system (see, for example, Non-Patent Document 2). In order to efficiently produce an alloprotein having a non-naturally occurring amino acid specifically introduced thereinto, it is inevitable to expand a genetic code system by modifying specificity of an aminoacyl-tRNA synthetase (hereinafter referred to as "aaRS") to tRNA or an amino acid.

As an expression method of such an alloprotein, a method for introducing a phenylalaninyl-tRNA synthetase•tRNA$^{Phe}$ pair from budding yeast into *E. coli*, thereby amber codon-specifically introducing p-fluorophenylalanine was first reported (see Non-Patent Document 3). At present, the expansion of a genetic code is successfully achieved in *E. coli* which is a eubacteria and in a eucaryote (see Non-Patent Document 4 regarding a wheat germ extract; and Non-Patent Document 5 regarding a mammalian cell). In all of these examples, a pair of a TyrRS mutant and an amber-suppressor tRNA$^{Tyr}$ is introduced. However, though a eubacteria type TyrRS•tRNA$^{Tyr}$ and an archaebacterium/eucaryote type TyrRS•tRNA$^{Tyr}$ are aminoacylated within each of the groups, it is the key that they are in an orthogonal relation that they cannot be aminoacylated between the groups each other. For example, since a TyrRS•tRNA$^{Tyr}$ pair of an archaebacterium *Methanococcus jannaschii* becomes an orthogonal pair in an *E. coli* system, whereas a pair of *E. coli* TyrRS and *Bacillus stearothermophilus* tRNA$^{Tyr}$ becomes an orthogonal pair in a mammalian cell system, they are used for the expansion of artificial genetic codes thereof (see, for example, Patent Document 1 and Non-Patent Document 5).

On the other hand, phosphoserine is one of amino acids playing a very important role for signal transduction or the like in living bodies. Phosphoserine is in general produced upon phosphorylation of a serine residue in a protein by a specific protein kinase within a mammalian cell. However, there has been no precedent in which this amino acid is successfully site-specifically introduced into a protein via translation during protein synthesis. A chief reason for this resides in the matter that it is difficult to design a modified aaRS capable of recognizing phosphoserine. However, in recent years, it has been reported that methanogenic archaebacteria have a phosphoseryl-tRNA synthetase which is an aaRS capable of recognizing phosphoserine (see, for example, Non-Patent Document 6). According to this, various methanogenic archaebacteria lack a cysteinyl-tRNA synthetase (CysRS), and instead of this, a synthesis route of Cys-tRNA$^{Cys}$ by a two-step reaction in which tRNA$^{Cys}$ is acylated with a phosphoseryl-tRNA synthetase (SepRS), and the produced phosphoseryl (Sep)-tRNA$^{Cys}$ is converted into Cys-tRNA$^{Cys}$ with a Sep-tRNA:Cys-tRNA synthetase is elucidated. All of the documents cited in this specification are incorporated herein by reference.

[Patent Document 1] WO 2004/070024
[Non-Patent Document 1] Hendrickson, W. A., et al., *The EMBO Journal*, 1990, Vol. 9, pp. 1665-72
[Non-Patent Document 2] Nowak M. W., et al., *Science*, 1995, Vol. 268, pp. 439-42
[Non-Patent Document 3] Furter, R., *Protein Science*, 1998, Vol. 7, pp. 419-26
[Non-Patent Document 4] Kiga, D., et al., *Proc Natl Acad Sci USA*, 2002, Vol. 99, pp. 9715-20
[Non-Patent Document 5] Sakamoto, K., et al., *Nucleic Acids Research*, 2002, Vol. 30, pp. 4692-4699
[Non-Patent Document 6] Sauerwald, A., et al., *Science*, 2005, Vol. 307, pp. 1969-1972

The entire disclosures of Patent Document 1 and Non-Patent Documents 1 to 6 are incorporated herein by reference thereto. The following analyses are given by the present invention.

DISCLOSURE OF THE INVENTION

1. Problems to be Solved by the Invention

However, according to the analysis made by the present inventors, it is not clear whether or not SepRS which the methanogenic archaebacterium has is able to bind phosphoserine (Sep) with the suppressor tRNA. Also, it is not clear whether or not SepRS of such an archaebacterium has orthogonality with an aaRS.tRNA pair of a *eubacterium* such as *E. coli*, etc. Accordingly, an object of the present invention is to prepare a mutant SepRS which is suitable for a method for the site-specific introduction of phosphoserine into a protein by analyzing the structure and functions of an archaebacterium-derived SepRS and develop a method for the site-specific introduction of phosphoserine using such a mutant SepRS and a suppressor tRNA.

2. Means to Solve the Problems

The present invention has been made for the purpose of solving the foregoing problems and successfully determined a three-dimensional structure of a SepRS-tRNA$^{Cys}$-phosphoserine ternary complex through an X-ray structural analysis thereof. It has been understood from the obtained structure that the SepRS exists as a homotetramer, with which two molecules of tRNA$^{Cys}$ bind; and that the SepRS recognizes each of three oxygen atoms of a phosphate group of phosphoserine by two hydrogen bonds. Also, it has been elucidated that the recognition of tRNA$^{Cys}$ by the SepRS is chiefly made by the hydrogen bond with a base of an anticodon loop, and on the basis of these structure, the present invention has been accomplished by designing and preparing a mutant SepRS capable of binding with a suppressor tRNA.

That is, in a first viewpoint, the mutant SepRS of the present invention is characterized in that in an amino acid sequence depicted in SEQ. ID NO:2, either one or both of glutamic acids at position-418 and position-420 are each composed of an amino acid sequence substituted with other amino acid and that the binding affinity with a suppressor tRNA is enhanced as compared with a wild type phosphoseryl-tRNA synthetase (SepRS) composed of an amino acid sequence depicted in SEQ. ID NO:2. It is preferable that the glutamic acids at position-418 and position-420 are each substituted with asparagine. In a more preferred exemplary embodiment, it is characterized in that in the amino acid sequence depicted in SEQ. ID NO:2, threonine at position-423 is substituted with a hydrophobic amino acid. It is further preferable that the hydrophobic amino acid is valine. In the mutant SepRS, a mutant SepRS composed of an amino acid sequence in which one or several amino acids at positions other than the position-418, position-420 and position-423 are deleted, substituted, or added, and having binding affinity with both of phosphoserine and the suppressor tRNA is also included in the present invention. In an even further preferred exemplary embodiment, the suppressor tRNA is an amber suppressor tRNA or an opal suppressor tRNA.

In some other viewpoints of the present invention, there are provided an isolated DNA for encoding the mutant SepRS, an expression vector containing the subject DNA and a *eubacterium* transformed by the subject expression vector.

In a separate viewpoint of the present invention, there is provided a method for producing a protein having phosphoserine integrated thereinto, which is characterized by expressing (a) an aminoacyl-tRNA synthetase relative to phosphoserine, (b) a suppressor tRNA capable of accepting phosphoserine in the presence of the aminoacyl-tRNA synthetase and (c) a gene for encoding a desired protein having been subjected to nonsense mutation or frameshift mutation at a desired position in the presence of phosphoserine within a cell or a cell extract.

In a further different viewpoint, there is provided a synthesis kit of a protein having phosphoserine integrated thereinto, which contains (a) a cell extract, (b) the mutant SepRS and (c) a suppressor tRNA capable of binding with phosphoserine in the presence of the mutant SepRS.

In a still further different viewpoint, the present invention is concerned with a screening method of a mutant SepRS capable of aminoacylating a suppressor tRNA with phosphoserine in a protein synthesis system of a *eubacterium*, which is characterized by including (a) selecting one or two or more amino acid residues of a SepRS which, on the basis of a three-dimensional structure of a complex between an archaebacterium-derived SepRS and tRNA$^{Cys}$, participates in an interaction with a base of an anticodon loop of the tRNA$^{Cys}$; (b) synthesizing a mutant SepRS in which the selected amino acid residue or residues are substituted with an amino acid; (c) measuring binding affinity of a wild type SepRS and the mutant SepRS with a suppressor tRNA; and (d) selecting the mutant SepRS having higher binding affinity with the suppressor tRNA than that of the wild type SepRS. It is preferable that the amino acid residue or residues selected in the step (a) are selected from glutamic acid residues at position-418 and position-420 and a threonine residue at position-423 in an amino acid sequence depicted in SEQ ID NO:2.

3. Meritorious Effects of the Invention

The mutant SepRS of the present invention is able to charge tRNA$^{Cys}$ with phosphoserine in a high efficiency. Also, though the wild type SepRS has activity to aminoacylate a tRNA mixture of *E. coli*, in the mutant SepRS of the present invention, such activity was suppressed on a very low level. Accordingly, a pair of a mutant SepRS and a suppressor tRNA of the present invention is able to be utilized for the site-specific introduction of phosphoserine into a protein and provides a novel preparation method of an alloprotein.

BRIEF DESCRIPTIONS OF THE DRAWINGS

The patent or application file contains at least one drawing executed in color. Copies of this patent or patent application publication with color drawing(s) will be provided by the office upon request and payment of the necessary fee.

FIG. 2 is a model drawing of recognition of phosphoserine (Sep) by a SepRS.

FIG. 4 is a graph showing phosphoserine binding activity to a wild type tRNA, an amber tRNA and an opal tRNA regarding wild type and various mutant SepRSs.

PREFERRED MODES FOR CARRYING OUT THE INVENTION

[Phosphoseryl-tRNA Synthetase (SepRS)]

Figure 1:
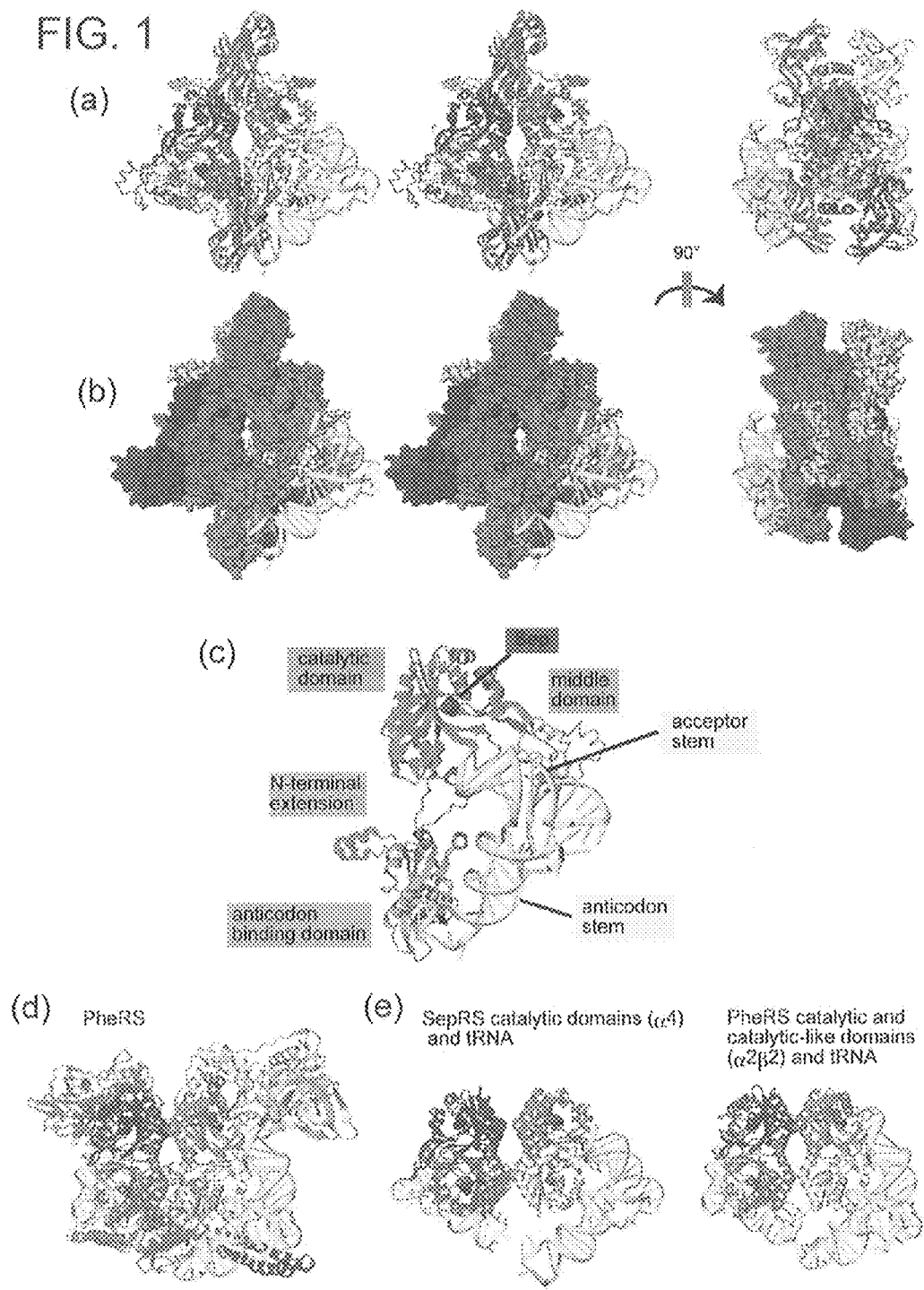
FIG. 1 is a model drawing showing the entire structure of a SepRS α tetramer in which a complex is formed together with two molecules of tRNA$^{Cys}$.

The phosphoseryl-tRNA synthetase (SepRS) according to the present invention can be prepared by introducing mutation by various methods on the basis of a wild type SepRS acquired from an archaebacterium, in particular a methanogenic archaebacterium. The wild type SepRS can be acquired from, for example, methanogenic archaebacteria such as *Methanosarcina mazei, Methanococcus maripaludis* and *Methanocaldococcus jannaschii*, sulfur-reducing archaebacteria such as *Archaeoglobus fulgidus*, and the like, but the present invention is not limited thereto. A number of genome base sequences of bacteria including these archaebacteria are publicly known. For example, by conducing homology search of a base sequence from a common database such as GenBank, etc., it is also possible to acquire other homologous genes. As typical examples, a SepRS derived from *Methanosarcina mazei* is registered as GenBank Accession No. NC_003901; a SepRS derived from *Methanococcus maripaludis* is registered as GenBank Accession No. NC_005791; a SepRS derived from *Methanocaldococcus jannaschii* is registered as GenBank Accession No. NC_000909; and a SepRS derived from *Archaeoglobus*

*fulgidus* is registered as GenBank Accession No. NC_000917 (Gene ID: 1483322). The SepRS derived from *Archaeoglobus fulgidus* is especially preferable, and a base sequence of its gene was depicted in SEQ ID NO:1, whereas an amino acid sequence of its protein was depicted in SEQ ID NO:2. The sequences of these SepRSs are well stored, and for example, the homology of the amino acid sequence is approximately 70% or more. The three-dimensional structures of these wild type SepRSs are analyzed, and the mutant SepRS of the present invention is prepared according to a method as described below in detail.

[tRNA]

A tRNA which is used in combination with the foregoing phosphoseryl-tRNA synthetase (SepRS) must meet requirements that it is allotted to a nonsense codon which is not a codon usually allotted to the 20 kinds of amino acids; and that it is recognized only by the subject SepRS but not recognized by a usual aminoacyl-tRNA synthetase of a host (orthogonal tRNA). Since the foregoing archaebacterium-derived SepRS makes phosphoserine bind with tRNA$^{Cys}$ corresponding to cysteine within such an archaebacterium, in order that the tRNA corresponding to the mutant SepRS binds to the mutant SepRS and functions as a suppressor tRNA, it must keep a three-dimensional structure analogous to the original archaebacterium-derived tRNA$^{Cys}$ and have a nonsense anticodon corresponding to a nonsense codon in place of a codon (TGC or TGT) corresponding to cysteine. That is, the tRNA is a suppressor tRNA which meets requirements that it is allotted to a nonsense codon which is not a codon usually allotted to the 20 kinds of amino acids; and that it is recognized only by the subject mutant SepRS but not recognized by a usual aaRS of a host (orthogonality).

Here, examples of the nonsense codon include UAG (amber), UAA (ocher) and UGA (opal), and it is preferable to use a UAG (amber) or UGA (opal) codon. Also, a codon composed of four or more bases (preferably four or five bases) (hereinafter referred to as "frameshift codon") can also be used in place of the nonsense codon.

Such a tRNA can be prepared by, for example, acquiring a gene corresponding to tRNA-Cys from the foregoing archaebacterium genome and introducing desired mutation thereinto. As an example, a wild type tRNA gene derived from *Archaeoglobus fulgidus* is registered as GenBank Accession No. NC_000917 (Gene ID: 1484681) and has a base sequence as described below.

```
AFtRNA-Cys-1:
                                              (SEQ ID NO: 3)
5'-GCCAGGGTGGCAGAGGGGCTATGCGGCGGACTGCAGATCCGCTTTAC

CCCGGTTCGAATCCGGGCCCTGGCT-3'
```

[Preparation of Mutant SepRS]

The present invention provides a mutant SepRS prepared on the basis of a three-dimensional structure of a SepRS-tRNA$^{Cys}$-phosphoserine ternary complex. Specific methods of crystallization of the subject ternary complex and its X-ray structural analysis are those described in the Examples as described below. A crystal of a ternary complex of a SepRS derived from a thermophilic sulfur bacterium (*Archaeoglobus fulgidus*), tRNA$^{Cys}$ and phosphoserine has a space group of P3$_1$21, and a unit cell thereof has a dimension of a b=149.12 angstroms and c=153.91 angstroms. The unit cell as referred to herein means the smallest and simple volume element of a crystal, and the space group as referred to herein means symmetry of the unit cell. Atomic coordinates of each of a SepRS-tRNA$^{Cys}$-Sep ternary complex and a SepRS-tRNA$^{Cys}$ binary complex obtained by resolution at 2.6 angstroms and 2.8 angstroms are registered as code numbers of 2DU3 and 2DU4, respectively in the Protein Data Bank (PDB, operated by The Research Collaboratory for Structural Bioinformatics (RCSB) <Reference 1>). The entire disclosure of the above Reference 1 is incorporated herein by reference thereto.

By elucidating the foregoing crystal structure, a binding mode between SepRS and tRNA$^{Cys}$ is estimated. Then, the present inventors have designed a mutant SepRS having enhanced binding affinity to tRNA$^{Cys}$ derivatives with amber and opal codons on the basis of this and confirmed its effectiveness. Thus, according to an exemplary embodiment of the present invention, there is provided a mutant SepRS composed of an amino sequence in which in an amino acid sequence depicted by SEQ ID NO:2, either one or both of glutamic acids at position-418 and position-420 are substituted with other amino acid, respectively. It is more preferable that threonine at position-423 of the subject mutant SepRS is substituted with a hydrophobic amino acid, preferably valine.

As a method for preparing such a mutant, various methods which are publicly known by a person skilled in the art can be employed. For example, by using a primer in which a base sequence for encoding a position of a desired amino acid is substituted with a base sequence for encoding an amino acid to be modified, it is possible to amplify a DNA having been substituted with a base sequence for encoding the amino acid to be modified by PCR to acquire a DNA for encoding the full-length mutant SepRS and express it using a host cell such as *E. coli*, etc. Alternatively, the preparation can be achieved by a publicly known site-specific mutation introduction method such as a Kunkel method, a gapped duplex method, etc., and a kit for the mutation introduction utilizing such a method (for example, Mutant-K and Mutant-G (TAKARA), etc.) can be utilized.

Furthermore, proteins composed of an amino acid sequence in which in the amino acid sequence which the foregoing mutant SepRS has, one or several amino acids at positions other than the position-418, position-420 and position-423 are deleted, substituted, or inserted, and having binding affinity with both of phosphoserine and the suppressor tRNA are included in the present invention. The terms "one or several amino acids" mean at most about 5 to 10% of the number of full-length amino acid residues, for example, from about 1 to 50, preferably from about 1 to 20, more preferably from about 1 to 10, and most preferably from about 1 to 5. Similarly, so far as mutant SepRSs have prescribed mutation at position-418, position-420 and position-423 in the foregoing amino acid sequence and keep desired activity, those having homology of 70% or more, preferably homology of 80% or more, and more preferably homology of 90% or more with respect to other amino acid residues are also included in the mutant SepRS of the present invention.

In a preferred exemplary embodiment of the present invention, it was acknowledged that a mutant SepRS in which glutamic acids at position-418 and position-420 of an amino acid sequence of a wild type SepRS are substituted with asparagine, respectively has high binding affinity with the foregoing two kinds of suppressor tRNAs. In this specification, the terms "high biding affinity" mean that the binding affinity between an anticodon binding domain of the SepRS and an anticodon of the suppressor tRNA is high, and it may be considered that the binding between the both is stabilized due to intermolecular electrostatic interactions or hydrogen bonds or various binding powers such as a Van der Waals force, etc. Such binding affinity can be detected by measuring the amount of phosphorylated tRNA (Sep-tRNA) formed by purifying the respective molecules and performing an in vitro enzymatic reaction in the presence of ATP and phosphoserine.

[DNA for Encoding the Mutant SepRS of the Present Invention, Expression Vector Containing the Subject DNA and Transformant]

Also, the present invention includes a DNA for encoding the above-obtained mutant SepRS. In a preferred exemplary embodiment, the DNA of the present invention is a DNA for encoding a wild type SepRS depicted in SEQ ID NO:1, in which codons (GAG) corresponding to glutamic acids at position-418 and position-420 are respectively substituted with a codon (AAT or AAC) corresponding to asparagine. Furthermore, it is more preferable that a codon (ACG) corresponding to threonine at position-423 is substituted with valine (GTT, GTC, GTA or GTG).

Also, the DNA of the present invention includes a DNA composed of a base sequence depicted in SEQ ID NO:1; and a DNA which when computed under a default condition using BLAST or the like, has homology of at least 80% or more, preferably 90% or more, and more preferably 95% or more and in which codons of amino chains at position-418 and position-420 are each composed of a codon corresponding to asparagine, and more preferably, a codon of an amino acid at position-423 for encoding valine. Furthermore, an RNA corresponding to the foregoing DNA, for example, an mRNA transcribed from the foregoing DNA or an antisense RNA or the like is included, too.

Also, a DNA which hybridizes with a DNA composed of a complementary sequence to the foregoing DNA under a stringent condition and which encodes a mutant SepRS having enhanced binding affinity with the suppressor tRNA as compared with a wild type phosphoseryl-tRNA synthetase (SepRS) is included in the DNA of the present invention. The terms "hybridizes under a stringent condition" as referred to herein mean an experimental condition which is well known by a person skilled in the art. Specifically, the "stringent condition" as referred to herein refers to a condition under which identification can be achieved by, after hybridization at 60 to 68° C. in the presence of from 0.7 to 1 M of NaCl, conducting rinsing with from 0.1 to 2 times of an SSC solution at 65 to 68° C. ("1×SSC" as referred to herein is composed of 150 mM of NaCl and 15 µM of sodium citrate). For the purpose of selecting the stringency, a salt concentration or temperature in the rinsing step can be properly optimized. Also, it is a technical common sense for a person skilled in the art to add formamide, SDS or the like for the purpose of increasing the stringency.

Also, the present invention includes an expression vector capable of expressing a mutant SepRS by coupling (inserting) the DNA of the present invention. The vector for inserting the DNA of the present invention is not particularly limited so far as it can be copied in a host, and examples thereof include a plasmid DNA and a phage DNA. It is preferable that when the expression vector of the present invention is introduced into a host cell, it is integrated into the vector such that it is able to produce the foregoing mutant SepRS within the subject host cell. Then, in the vector of the present invention, in addition to promoters (for example, a trp promoter, a lac promoter, a PL promoter, a tac promoter, etc.), ones containing a cis-element such as an enhancer, etc., a splicing signal, a poly A-added signal, a selection marker, a ribosome-binding sequence (SD sequence), etc. can be coupled, if desired. Examples of the selection marker include a dihydrofolate reductase gene, an ampicillin-resistant gene and a neomycin-resistant gene.

A transformant obtained by transformation using the expression vector of the present invention, preferably a prokaryotic cell or a eukaryotic cell is also included in the present invention. Examples of the *eubacterium* include eubacteria belonging to the *Escherichia* genus such as *Escherichia coli*, etc.; the *Bacillus* genus such as *Bacillus subtilis*, etc.; the *Pseudomonas* genus such as *Pseudomonas putida*, etc.; and the *Rhizobium* genus such as *Rhizobium meliloti*, etc. Also, examples of the eukaryotic cell include yeasts such as *Saccaromyces cerevisiae, Schizosaccharomyces pombe*, etc.; and animal cells such as COS cells, CHO cells, etc. As to the transformation method, the transformation can be carried out by a publicly known method, for example, a method using a calcium ion (Cohen, S. N., et al., (1972), *Proc. Natl. Acad. Sci., USA,* 69, 2110-2114<Reference 2>), a DEAE-dextran method, an electroporation method, etc. The entire disclosure of the above Reference 2 is incorporated herein by reference thereto.

[Production of Protein Having Phosphoserine Integrated Thereinto]

The thus obtained mutant SepRS can be used in combination with the suppressor tRNA of an archaebacterium or eukaryote for the in vitro or in vivo production of a protein having phosphoserine integrated thereinto. That is, there is provided a method for producing a protein having phosphoserine integrated thereinto, which is characterized by expressing (a) an aminoacyl-tRNA synthetase relative to phosphoserine, (b) a suppressor tRNA capable of accepting phosphoserine in the presence of the aminoacyl-tRNA synthetase and (c) a gene for encoding a desired protein having been subjected to nonsense mutation or frameshift mutation at a desired position in the presence of phosphoserine within a cell or a cell extract. Here, the synthesis system of the SepRS or suppressor tRNA is not particularly limited, and an arbitrary expression system can be used. Examples thereof include a cell-free protein synthesis system and a protein synthesis system within a eubacterial cell.

The cell-free protein synthesis system as referred to herein is a system for synthesizing a protein for the purpose of taking out a protein factor necessary for the translation of a protein as a cell extract and in vitro reconstituting this reaction. The cell-free system can be constituted utilizing an extract derived from a biospecies of every sort. For example, extracts of eukaryotic cells or prokaryotic cells in the state of high protein synthesis activity, such as bacteria such as *E. coli*, thermophilic bacteria, etc., wheat germs rabbit reticulocytes, mouse L-cells, Ehrich ascites tumor cells, HeLa cells, CHO cells, budding yeasts, etc. can be used (Clemens, M. J., *Transcription and Translation—A Practical Approach*, (1984), pp. 231-270; Henes, B. D., et al. eds., IRL Press, Oxford <Reference 3>). The entire disclosure of the above Reference 3 is incorporated herein by reference thereto.

As the extract of *E. coli*, an S30 extract prepared by a method described in Zubay, et al., *Ann. Rev. Genet.*, Vol. 7, pp. 267-287 (1973) <Reference 4> or Pratt, J. M., et al., *Transcription and Translation—A Practical Approach*, (1984), pp. 179-209; Henes, B. D., et al. eds., IRL Press, Oxford <Reference 5> can be used. The S30 extract of *E. coli* contains all of yeasts and factors of *E. coli* necessary for the transcription and translation. Furthermore, a supplementary mixed solution can be added. As to a specific preparation method, *E. coli* is first cultured, and bacterial cells are recovered by means of centrifugation, etc. After rinsing, the recovered bacterial cells are resuspended in a buffer and pulverized using a French press, glass beads, a Waring blender, etc. Insoluble substances of the pulverized *E. coli* are removed by means of centrifugation, the residue is mixed with a preincubation mixed solution, and the mixture is subjected to incubation. According to this operation, though intrinsic DNA and RNA are decomposed, an intrinsic nucleic acid may be further decomposed by the addition of a calcium salt, a nuclease of a *micrococcus*, etc. Subsequently, the intrinsic amino acids, nucleic acids and nucleotides and so on are removed by means of dialysis, and the residue is aliquoted into an every appropriate amount and stored by liquid nitrogen or at −80° C. The entire disclosures of the above References 4 and 5 are incorporated herein by reference thereto In carrying out a synthesis reaction of a protein having phosphoserine integrated thereinto, the foregoing cell extract can contain a DNA or RNA for encoding a desired protein having been subjected to nonsense mutation or frameshift mutation at a desired position which will become a transcription/translation template, a phosphoserine-containing amino acid, a mutant SepRS of the present invention, a suppressor tRNA capable of accepting phosphoserine in the presence of the foregoing mutant SepRS, an energy source, an ion of every sort, a buffer, an ATP regeneration system, a nuclease inhibitor, a tRNA, a reducing agent, polyethylene glycol, a cAMP, a folic acid and an antibacterial agent, and also, in case of using a DNA as a template, a substrate of RNA synthesis, an RNA polymerase, etc. These are properly selected and prepared depending upon the kind of a desired protein or a protein synthesis system to be used. For example, in case of an S30 extract of *E. coli*, a part or the whole of Tris-acetic acid, DTT, NTPs (ATP, CTP, GTP and UTP), phosphoenolpyruvic acid, pyruvate kinase, amino acids (added with phosphoserine in addition to the 20 kinds of naturally occurring amino acids), polyethylene glycol (PEG), folic acid, a cAMP, a tRNA, ammonium acetate, potassium acetate, potassium glutamate, and an optimal concentration of magnesium acetate, etc. are added.

Furthermore, the present invention provides a synthesis kit of a protein having phosphoserine integrated thereinto, which contains (a) the cell extract, (b) a mutant SepRS according to the present invention and (c) a suppressor tRNA capable of accepting phosphoserine in the presence of the mutant SepRS. In addition to this, it is preferable that an amino acid mixture of phosphoserine and a naturally occurring amino acid. By aliquoting such a constitutional element into an every fixed amount such that it is easily used, it can be delivered as a synthesis kit of a protein having phosphoserine integrated thereinto. Such a product can be stored in a frozen or dried state, accommodated in a container suitable for storage and transportation and sold as a kit. The kit can be attached with a user's manual, a positive control DNA, a vector DNA, etc.

EXAMPLES

1. Method:
[Preparation of Protein and tRNA]

A full-length SepRS gene derived from a thermophilic sulfur bacterium (*Archaeoglobus fulgidus*) was cloned into a plasmid pET26b (Novagen) utilizing restriction enzyme cleavage sites NdeI and SalI. The introduction of mutation was carried out employing a PCR method. Wild type and mutant enzymes were each excessively expressed using an *E. coli* BL21 codon plus (DE3) strain (Stratagene). A SepRS protein was thermally treated at 80° C. for 30 minutes and purified by means of column chromatography using Q-Sepharose FF (GE Healthcare) and unoQ (Bio-Rad). The purified enzyme was dialyzed against a Tris hydrochloride buffer (pH 8.0) containing 5 mM of magnesium chloride, 150 mM of sodium hydrochloride and 5 mM of β-mercaptoethanol and concentrated to about 9 mg/mL. A selenomethionine-labeled protein was excessively expressed using an *E. coli* B834 codon plus (DE3) strain and purified in the same method as in the naturally occurring enzyme. A tRNA$^{Cys}$ derived from *A. fulgidus* and a suppressor tRNA were each synthesized by an in vitro transcription reaction with a T7 RNA polymerase by cloning at HindIII and BamHI sites of a plasmid pUC119 upon addition of a T7 promoter sequence in the upstream of these genes and using them as a template. The transcribed tRNA was treated with phenol/chloroform and then purified by means of column chromatography using Resource Q (GE Healthcare). As to the tRNA, an L anticodon GCA of the tRNA$^{Cys}$ derived from *A. fulgidus* was substituted with UCA (tRNA$^{Cys}$ opal) or CUA (tRNA$^{Cys}$ amber).

[Crystallization]

The SepRS and the tRNA$^{Cys}$ were mixed in a molar ratio of 1/1.1 under a condition that a final SepRS concentration reached 6 to 8 mg/mL. In order to crystallize a ternary complex, 100 mM of phosphoserine (Sep) solution was added in the foregoing mixture, thereby regulating the final concentration at 2 mM. A SepRS-tRNA$^{Cys}$ binary complex and a SepRS-tRNA$^{Cys}$-Sep ternary complex were each grown at 20° C. by a hanging-drop vapor-diffusion method. A 1-μL sample was mixed with 1 μL of a reservoir solution (8% of PEG6000 and 1.2 M of sodium hydrochloride).

[Structural Analysis]

A selenomethionine-introduced SAD (SepRS-tRNA$^{Cys}$-Sep) data set and a native data set (SepRS-tRNA$^{Cys}$-Sep and SepRS-tRNA$^{Cys}$) were acquired by the beam line BL41XU of Spring-8. The collected data was processed using HKL2000. The structure was determined using a Se-SAD data set and SnB and Mlphare. The correction of an electron density was carried out using DM. Repetitive model construction using QueMol and refinement by CNS were carried out several times. An asymmetric unit of the crystal contained two molecules of SepRS and one molecule of tRNA$^{Cys}$. The electron density corresponding to from residue 105 to residue 173 of the SepRS molecule B and the electron density corresponding to the last 4 nucleotide residues of the tRNA, Uri73-Cyt74-Cyt75-Ade76 were disordered.

[Phosphoserine Binding Assay to tRNA]

A phosphoserine charging reaction to tRNA was carried out at 50° C. for 10 minutes in 100 mM of an HEPES-NaOH buffer (pH 7.6) containing 20 mM of magnesium chloride, 150 mM of sodium chloride, 5 mM of ATP, 60 μM of $^{14}$C-labeled phosphoserine, 1 μM of a SepRS enzyme and 20 μM of in vitro transcribed tRNA$^{Cys}$ or suppressor tRNA. After elapsing a prescribed period of time, a fixed amount of a sample was taken out from the reaction mixture, and the reaction was stopped on filter paper (Whatman 3 mm) having been equilibrated with 10% trichloroacetic acid (TCA). The filter paper was rinsed with a 5% ice-cooled TCA solution three times and subsequently rinsed with 100% ethanol one time. Radioactivity of a precipitate on the filter paper was measured by a scintillation counter.

2. Results:

Crystal structures of each of the thermophilic sulfur bacterium (*Archaeoglobus fulgidus*)-derived SepRS-tRNA$^{Cys}$-Sep ternary complex and the SepRS-tRNA$^{Cys}$ binary complex obtained by resolution at 2.6 angstroms and 2.8 angstroms are shown in FIG. 1. The SepRS was shown by a ribbon model in (a) of FIG. 1 and a surface model in (b) of FIG. 1, respectively. The tRNA$^{Cys}$ was shown by a yellow tube, and the Sep molecule was shown by a reddish purple CPK model. In this structure, the SepRS forms a tetramer of α4, and the four subunits are tangled with each other ((a) and 1(b) of FIG. 1). The two molecules of the tRNA$^{Cys}$ are bound with the SepRS tetramer. In the ternary complex, the phosphoserine (Sep) molecule is bound with all of the four active center sites of the SepRS tetramer. A SepRS monomer is composed of four portions which are an extending portion on the N-terminal side (blue residues 1 to 45), a catalyst domain (green residues 46 to 99), a central domain (orange residues 100 to 177) and an anticodon-binding domain on the C-terminal side (pink residues 355 to 534) ((c) of FIG. 1). It is perceived that these four portions are linked via a linker loop, and any two of the four portions do not F substantially come into contact with each other. Instead thereof, it may be considered that they are widely brought into contact with other subunits of the tetramer, thereby contributing to the formation of a stable α4 tetramer. As a result of ultracentrifugation for analysis, it was explicitly demonstrated that the SepRS derived from *A. fulgidus* and the SepRS derived from *Methanocaldococcus jannaschii* formed an α4 tetramer in the solution (not shown by a data).

Among the aminoacyl-RNA synthetases, the α4 structure has been first elucidated by the present inventors. Aminoacyl-RNA synthetases of the classes Ia and Ib form a monomer. Aminoacyl-RNA synthetases of the classes Ic, IIa and IIb usually form an α2 dimer (exceptionally, some alanyl-tRNA synthetases (AlaRS) form an α4 tetramer; and some glycyl-tRNA synthetases (GlyRS) form an α2β2 tetramer). PheRS which is only one member of an aminoacyl-RNA synthetase of the class II among the 20 kinds of regular aminoacyl-RNA synthetases forms an α2β2 tetramer ((d) of FIG. 1) (a PheRS of mitochondria is a monomer). An α-subunit of the PheRS (shown by blue and yellow colors in (d) of FIG. 1) contains a catalyst domain, and a β-subunit (shown by sky blue and grey colors in (d) of FIG. 1) contains a catalyst-like domain. Though this β-subunit has high structural similarity to the α-subunit, it is inactive. As expected from the similarity of the amino acid sequence, the structure of the SepRS catalyst domain has high homology with the structure of the catalyst domain of the PheRS ((e) of FIG. 1). Furthermore, the constitutions of the four catalyst domains of the SepRS α4 tetramer are similar to those of the catalyst of the α2β2 tetramer and the catalyst-like domain of the PheRS. In addition, the orientation of two bound tRNAs relative to the four domains (shown by a yellow color in (d) of FIG. 1) is similar between the SepRS and the PheRS. In addition to phylogenetic analysis, the similarity therebetween suggests that the SepRS and the PheRS have a common ancestor for forming an α4 tetramer. After branching of the ancestor type SepRS and PheRS, two of the four subunits of the PheRS lost catalytic activity and became a β-subunit. Taking into consideration the matter that all of publicly known PheRSs in the three kingdoms on the taxonomy exclusive of mitochondria form an α2β2 tetramer, the SepRS is a considerably old enzyme which has already existed since the ubiquitous ancestor type era. One tRNA$^{Cys}$ molecule is different from publicly known α2 dimer aminoacyl-tRNA synthetases or a PheRS in which a tRNA is bound crossing a subunit and comes into contact with only one SepRS monomer. It may be considered that this difference is caused due to the matter that the anticodon-binding domain is lately added during the process of evolution.

The catalyst domain recognizes the Sep in a deep cleft of the active site without causing significant conformation change (FIG. 2). (a) of FIG. 2 three-dimensionally depicts active sites of the Sep molecule-free SepRS-tRNA$^{Cys}$ binary complex; and (b) of FIG. 2 three-dimensionally depicts active sites of the SepRS-tRNA$^{Cys}$-Sep ternary complex. A phosphate moiety is closely recognized; and all of three oxygen atoms are recognized by two hydrogen bonds. One oxygen atom is hydrogen bonded to a side chain of Thr188 and a main chain NH of Thr188. Another hydrogen bond is a main chain NH of Met187 and a side chain of Ser231. The other hydrogen bond is a side chain of each of Ser233 and Asn325. A positively charged side chain does not recognize a negatively charged phosphate moiety. An α-$NH_3^+$ group of the Sep is hydrogen bonded to a side chain of each of Thr188 and Asn325. An α-$COO^-$ group of the Sep is hydrogen bonded to a side chain of each of His186 and Thr305. This close recognition of the Sep explains specificity that the SepRS recognizes the Sep but not the 20 kinds of regular amino acids.

Figure 3:
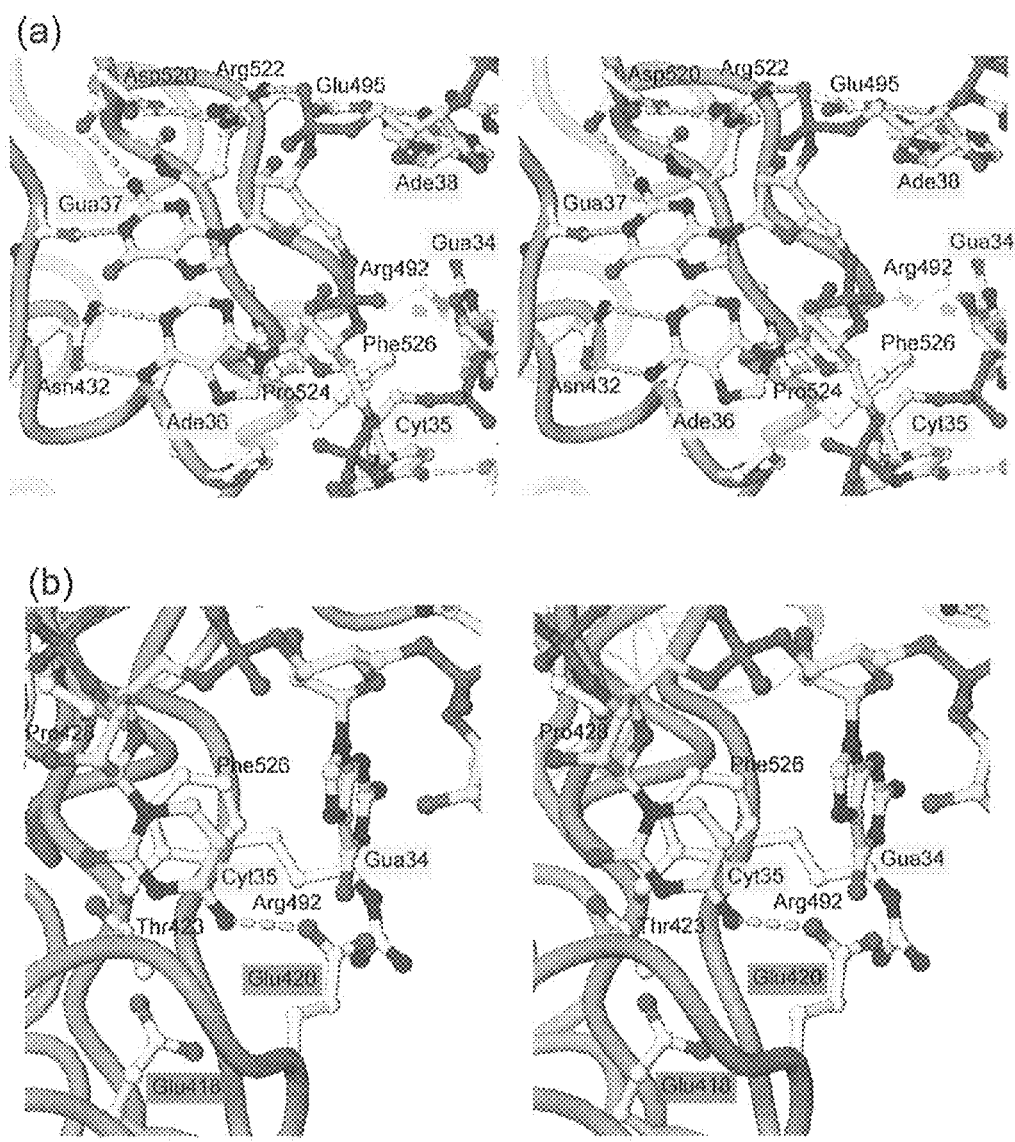
FIG. 3 is a model drawing of recognition of an anticodon loop by a SepRS.

The SepRS persistently recognizes the tRNA$^{Cys}$ upon contact with a tRNA anticodon loop ((c) of FIG. 1). FIG. 3 is a model drawing of recognition of an anticodon loop by a SepRS. (a) of FIG. 3 three-dimensionally depicts a recognition model of Ade36, Gua37 and Ade38; and (b) of FIG. 3 depicts a recognition model of Gua34 and Cyt35. A nucleotide of the anticodon loop is withdrawn upon contact with the anticodon-binding domain. A base of Gua34 which is a first nucleotide of an anticodon triplet is not directly hydrogen bonded in the crystal structure (FIG. 3). For example, a water molecule which is not seen in the resolution at 2.6 angstroms may possibly be recognized via the Gua34 base by side chains of Glu420 and Arg492. This is suggested by the following experiment of mutation introduction. The Cyt35 base is hydrogen bonded to the side chain of Glu420. A side chain of Phe526 is superimposed on the Cyt35 base. A side chain of Glu418 will participate in the recognition via the water molecule, too. An Ade36 base is hydrogen bonded to a side chain of Asn432. A Gua37 base is hydrogen bonded to CO of the mainchain of each of Gly443 and Asp520. An Ade38 base is hydrogen bonded to a side chain of Glu495. All of these observed base recognition modes are sequence-specific.

For the purpose of establishing a site-specific introduction system of phosphoserine using a suppression method, the present inventors prepared two suppressor tRNAs by substituting an anticodon sequence GCA derived from *A. fulgidus* with CUA (tRNA$^{Cys}$ amber) and UCA (tRNA$^{Cys}$ opal), respectively. However, the wild type SepRS did not phosphorseylate either of the tRNA$^{Cys}$ amber or F the tRNA$^{Cys}$ opal (FIG. 4). This demonstrates that though the Gua34 base is not perceived to have a direct interaction from the crystal structure, it is recognized by the SepRS ((b) of FIG. 3). Then, for the purpose of acquiring a mutant SepRS capable of phosphorylating the tRNA$^{Cys}$ amber and the tRNA$^{Cys}$ opal, two residues (Glu418 and Glu420) were selected and subjected to mutation introduction. These two Glu residues are conserved among the SepRSs. Glu418 will participate in the recognition of the Cyt35 base via the water molecule. Glu420 recognizes the Cyt35 base and will participate in the recognition of the Gua34 base via the water molecule, too. When mutation is introduced into any one of these residues, the phosphorylation activity of the wild type tRNA$^{Cys}$ was influenced to a greater or lesser degree (FIG. 4). FIG. 4 shows the phosphoserylation activity of wild type and various mutant SepRSs against the wild type tRNA$^{Cys}$, the tRNA$^{Cys}$ amber and the tRNA$^{Cys}$ opal. This result demonstrates that these residues actually participate in the recognition of the tRNA$^{Cys}$. One mutant enzyme (E418N/E420N) exhibited significant phosphoserylation activity against both of the tRNA$^{Cys}$ amber and the tRNA$^{Cys}$ opal. In this E418N/E420N mutant enzyme, the phosphoserylation activity toward the wild type tRNA$^{Cys}$ was enormously reduced.

Figure 5:
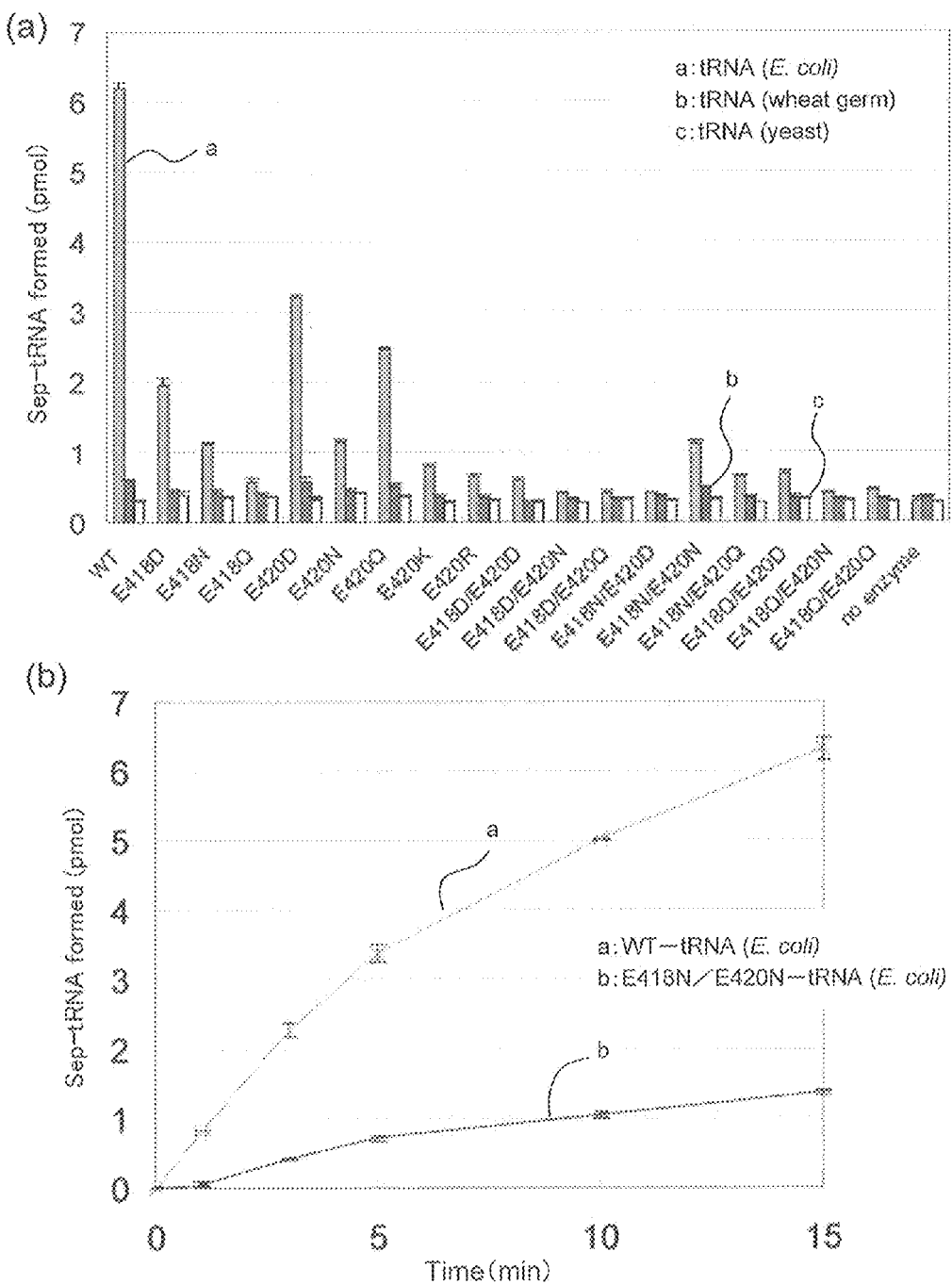
FIG. 5 is a graph showing phosphoserine binding activity to a tRNA mixture of *E. Coli*, wheat germ and yeast regarding wild type and various mutant SepRSs.

On the other hand, FIG. 5 shows the phosphorylation activity of wild type and various mutant SepRSs against a tRNA mixture from each of *E. coli*, wheat germ and yeast. Though the wild type SepRS exhibits phosphorylation activity against a tRNA mixture from *E. coli*, it does not exhibit phosphorylation activity against a tRNA mixture from wheat germ or yeast so that it is not preferable for the site-specific introduction of phosphoserine. However, such non-preferable activity was reduced in the SepRS mutant yeast (E418N/E420N). The E418N/E420N mutant was enormously reduced in the phosphorylation activity against a tRNA mixture of *E. coli* as compared with the wild type SepRS.

Furthermore, the present inventors prepared crystals of mutant SepRS (E418N/E420N)-tRNA$^{Cys}$ opal-Sep (opal complex) and mutant SepRS (E418N/E420N)-tRNA$^{Cys}$ amber-Sep (amber complex) and analyzed each of the crystals for an X-ray crystal structure by resolution at 3.2 angstroms and 3.3 angstroms, respectively. Atomic coordinates of these are registered as code numbers of 2DU5 and 2DU6, respectively in the Protein Data Bank. As a result, as shown in (a) of FIG. 6, in the opal complex, a side chain of Asn420 having a mutant SepRS substituted therewith was hydrogen bonded to $NH_4$ at position-4 of a pyridine ring of the C35 base. Though U34 having a tRNA$^{Cys}$ opal substituted therewith does not have a direct interaction to the mutant SepRS, a CO group as a side chain of Asn420 will be indirectly hydrogen bonded to 0 at position-4 of a pyridine ring of U34 via a non-observed water molecule. A side chain of Asn418 having a mutant SepRS substituted therewith was hydrogen bonded to a CO group of each of Lys424 and Leu425 as a main chain.

Figure 6:
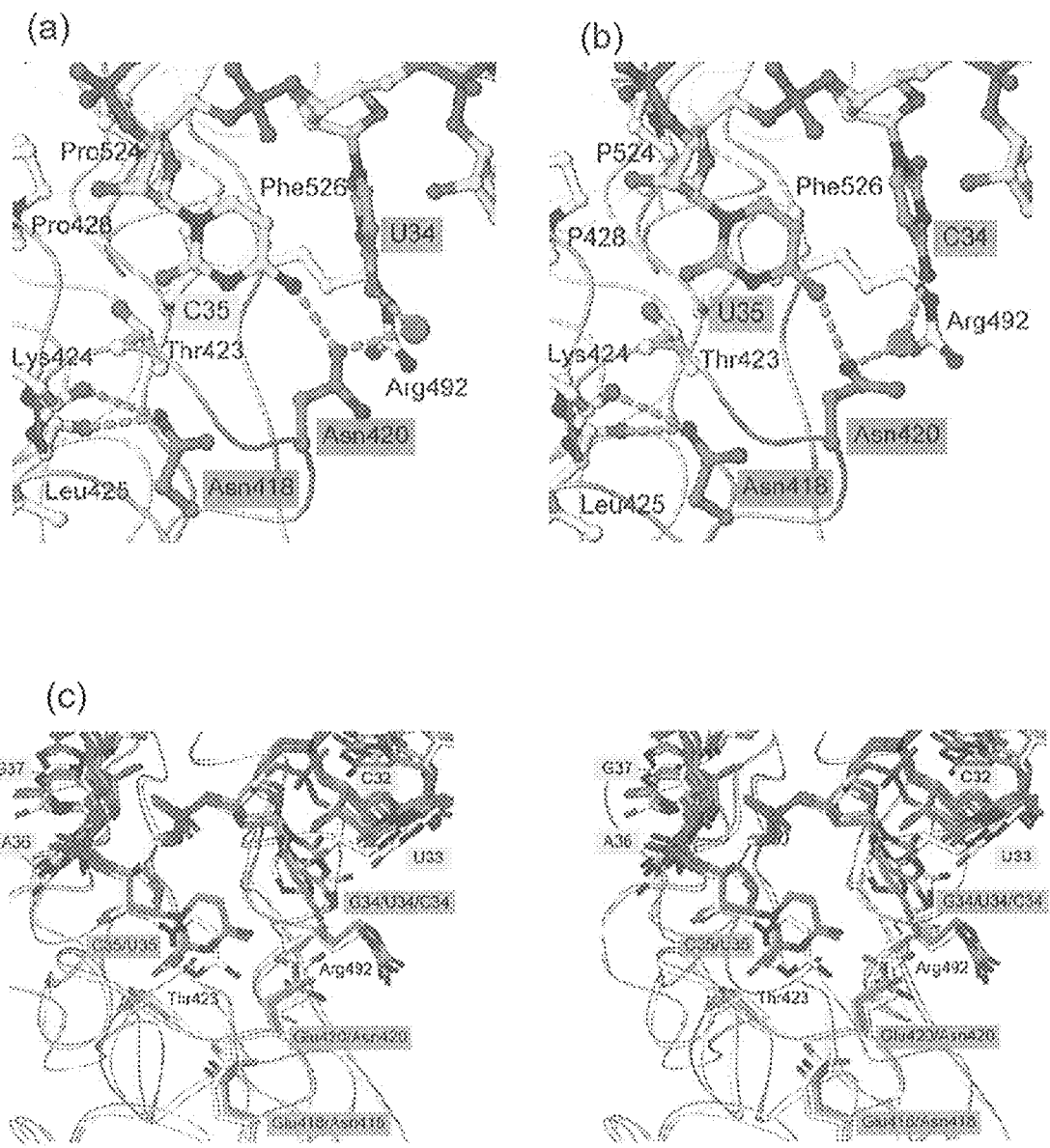
FIG. 6 is a model drawing of recognition of a suppressor tRNA ((a): opal, (b): amber) and a three-dimensional image (c) in which a wide type and opal and amber complexes are superimposed.

On the other hand, as shown in (b) of FIG. 6, in the amber complex, a side chain of Asn420 having a mutant SepRS substituted therewith was hydrogen bonded to O at position-4 of a pyridine ring of the U35 base. The side chain of Asn420 will be indirectly hydrogen bonded to the substituted C34 base via a non-observed water molecule. Similar to the opal complex, a side chain of Asn418 having a mutant SepRS substituted therewith was hydrogen bonded to a CO group of each of Lys424 and Leu425 as a main chain. In the light of the above, it may be considered that the mutant SepRS (E418N/E420N) could recognize both of the tRNA$^{Cys}$ opal and the tRNA$^{Cys}$ amber by changes of the conformation of the side chain of substituted Asn420. (c) of FIG. 6 shows a three-dimensional image in which complexes of the wild type, opal and amber tRNAs are superimposed. The conformation of tRNAs at position-32 to position-36 of the wild type complex is different from all of those of the opal and the amber. A side chain of Glu420 of the wild type SepRS will collide with 0 at position-4 of a pyridine ring of U34 of the tRNA$^{Cys}$ opal and O at position-4 of a pyridine ring of the U35 base of the tRNA$^{Cys}$ amber, respectively. Such a collision L (steric hindrance) will be caused due to the matter that the wild type SepRS cannot recognize the tRNA$^{Cys}$ opal and the tRNA$^{Cys}$ amber.

Figure 7:
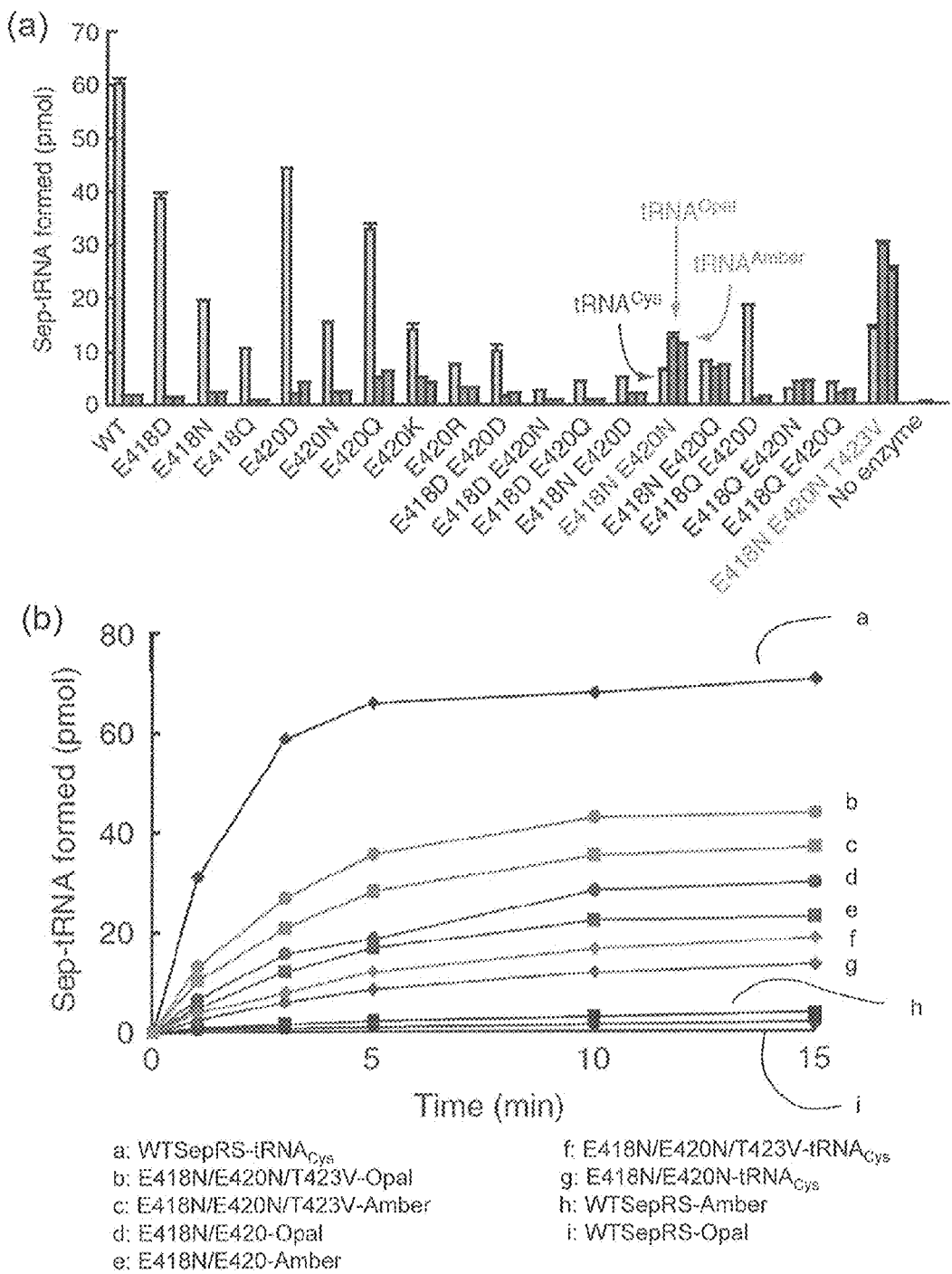
FIG. 7 is a graph showing phosphoserine binding activity to a wild type tRNA, an amber tRNA and an opal tRNA regarding various mutant SepRSs containing a wild type and a triple mutant.
Figure 8:
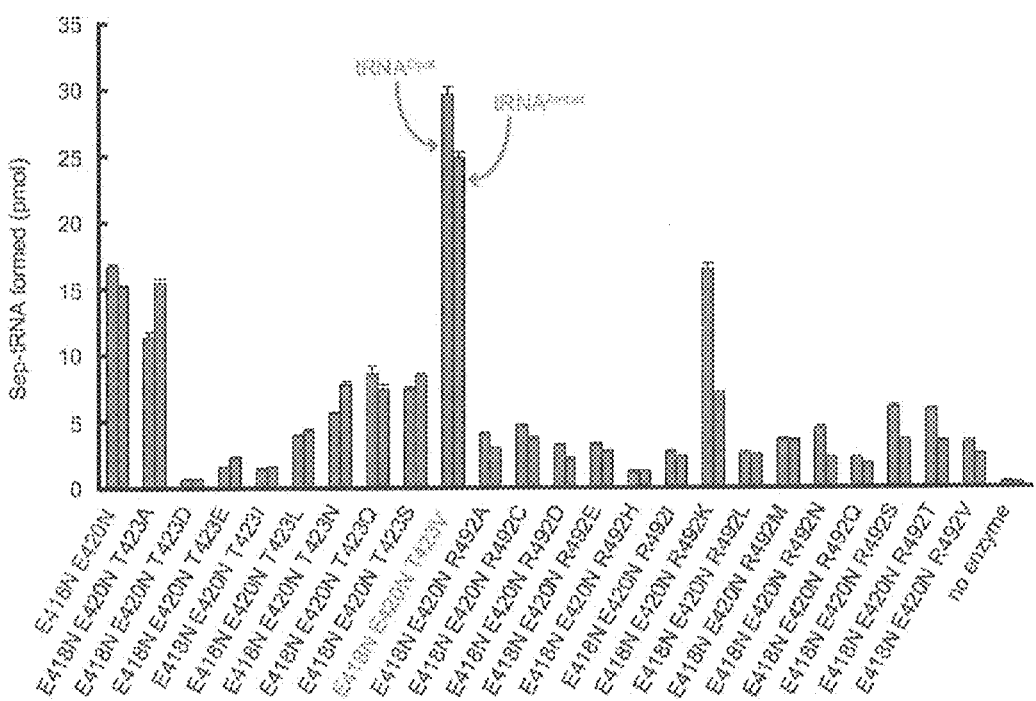
FIG. 8 is a graph showing phosphoserine binding activity of various triple mutant SepRSs in which additional mutation is further introduced into an E418N/E420N mutant.

On the basis of the structure of the complex with the foregoing suppressor tRNA, the present inventors attempted to achieve more efficient construction of a mutant SepRS by further introducing additional mutation into a threonine residue at position-1-423 and an arginine residue at 492-position of the mutant SepRS (E418N/E420N). FIG. 8 is a graph showing phosphoserine charging activity of various triple mutant SepRSs as thus prepared against the tRNA$^{Cys}$ opal or tRNA$^{Cys}$ amber. As a result, an E418N/E420N/T423V triple mutant exhibited higher phosphoserrylation activity against both of the opal and amber suppressor tRNAs than an E418N/E420N double mutant (see (a) of FIG. 7). It is estimated that a side chain of hydrophobic valine at position-423 of the SepRS is easy to recognize the substituted base at position-35 of the suppressor tRNA as compared with a side chain of hydrophilic threonine. (b) of FIG. 7 shows a change with time of phosphoserylation activity of the wild type, E418N/E420N double mutant and E418N/E420N/T423V triple mutant SepRSs toward the tRNA$^{Cys}$, the tRNA$^{Cys}$ opal and the tRNA$^{Cys}$ amber. From the results thereof, the phosphoserylation activity (initial rate and maximum value) of the E418N/E420N/T423V triple mutant SepRS toward the tRNA$^{Cys}$ opal and the tRNA$^{Cys}$ amber were about 30% (initial rate) and about 60% (maximum value), respectively as compared with that toward the tRNA$^{Cys}$ of the wild type SepRS.

Figure 9:
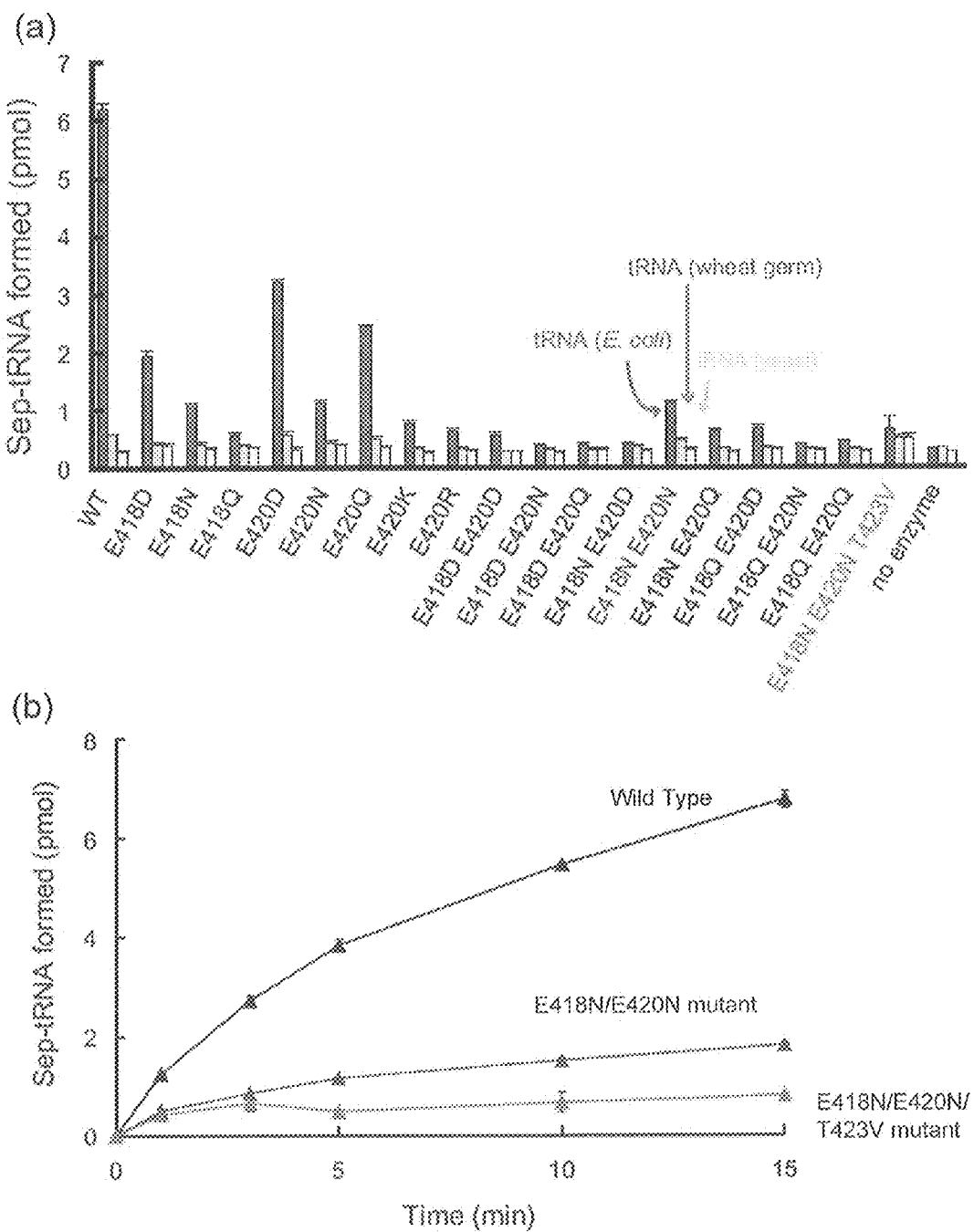
FIG. 9 is a graph showing phosphoserine binding activity to a tRNA mixture of *E. coli*, wheat germ and yeast regarding various mutant SepRSs containing a wild type and a triple mutant.

Furthermore, (a) of FIG. 9 shows phosphoserylation activity of wild type and various mutant SepRSs toward a tRNA mixture from each of *E. coli*, wheat germ and yeast. The E418N/E420N/T423V triple mutant SepRS did not substantially react with any of the foregoing tRNA mixtures and was significantly reduced in the phosphoserylation activity toward the *E. coli* tRNA mixture as compared with the double mutant enzyme (E418N/E420N). This result was also confirmed from the measurement result ((b) of FIG. 9) of a change with time of the phosphoserylation activity toward the *E. coli* tRNA mixture.

From the foregoing results, a pair of a mutant SepRS (E418N/E420N/T423V) and a tRNA$^{Cys}$ amber or a tRNA$^{Cys}$ opal is extremely useful for the site-specific introduction of phosphoserine residue into a protein.

The matters disclosed in the Examples of this specification are described by the present inventors in a publication, *Nature Structural & Molecular Biology*, Vol. 14, No. 4, pp. 272-279 (2007), the entire contents of which are incorporated herein by reference.

It should be noted that changes and modifications of the exemplary embodiments or Examples may be done within the entire disclosure (inclusive of the claims) of the present invention and on the basis of basic technical thoughts thereof. Also, it should be noted that any combination of various disclosed elements may be made within the scope of the claims of the present invention.

The invention claimed is:

1. A mutant phosphoseryl-tRNA synthetase (SepRS), comprising an amino acid sequence that is at least 90% identical to SEQ ID NO: 2 wherein the amino acid sequence has at least one of the following modifications: E418N, E420D, E420N, E420Q, E420K, E420R, E418N and E420D, E418N and E420N, E418N and E420Q, E418Q and E420N or E418Q and E420Q, and wherein the binding affinity of said mutant SepRS to a suppressor tRNA is higher than the binding affinity of a wild type SepRS having the amino acid sequence depicted in SEQ ID NO: 2 to the suppressor tRNA.

2. The mutant SepRS according to claim 1, wherein the glutamic acids at position-418 and position-420 are each substituted with asparagine.

3. The mutant SepRS according to claim 1, wherein the threonine at position-423 is substituted with a hydrophobic amino acid.

4. The mutant SepRS according to claim 3, wherein the hydrophobic amino acid is valine.

5. The mutant SepRS according to claim 1, in which one or several amino acids at positions other than the position-418, position-420 and position-423 are deleted, substituted or are added and wherein said mutant SepRS has binding affinity to both of phosphoserine and the suppressor tRNA.

6. The mutant SepRS according to claim 1, wherein the suppressor tRNA is an amber suppressor tRNA or an opal suppressor tRNA.

7. An isolated DNA for encoding a mutant phosphoseryl-tRNA synthetase (SepRS), comprising an amino acid sequence that is at least 90% identical to SEQ ID NO: 2, wherein the amino acid sequence has at least one of the following modifications: E418N, E420D, E420N, E420Q, E420K, E420R, E418N and E420D, E418N and E420N, E418N and E420Q, E418Q and E420N or E418Q and E420Q, and wherein the binding affinity of said mutant phosphoseryl-tRNA synthetase to a suppressor tRNA is higher than the binding affinity of a wild type phosphoseryl-tRNA synthetase (SepRS) having the amino acid sequence depicted in SEQ ID NO: 2 to the suppressor tRNA.

8. An expression vector comprising a polynucleotide encoding a mutant phosphoseryl-tRNA synthetase (SepRS), comprising an amino acid sequence that is at least 90% identical to SEQ. ID NO:2, wherein the amino acid sequence has at least one of the following modifications: E418N, E420D, E420N, E420Q, E420K, E420R, E418N and E420D, E418N and E420N, E418N and E420Q, E418Q and E420N or E418Q and E420Q, and wherein the binding affinity of said mutant phosphoseryl-tRNA synthetase to a suppressor tRNA is higher than the binding affinity of a wild type phosphoseryl-tRNA synthetase (SepRS) having the amino acid sequence depicted in SEQ ID NO: 2 to the suppressor tRNA, wherein said vector is operatively linked to an expression control sequence and expresses said mutant SepRS when introduced in a host cell.

9. A eubacterium host cell that is transformed with an expression vector that comprises a polynucleotide encoding a mutant phosphoseryl-tRNA synthetase (SepRS), comprising an amino acid sequence that is at least 90% identical to SEQ ID NO: 2, wherein the amino acid sequence has at least one of the following modifications: E418N, E420D, E420N, E420Q, E420K, E420R, E418N and E420D, E418N and E420N, E418N and E420Q, E418Q and E420N or E418Q and E420Q, and wherein the binding affinity of said mutant phosphoseryl-tRNA synthetase to a suppressor tRNA is higher than the binding affinity of a wild type phosphoseryl-tRNA synthetase (SepRS) having the amino acid sequence depicted in SEQ. ID NO: 2 to the suppressor tRNA wherein said expression vector is operatively linked to an expression control sequence and is capable of producing the mutant SepRS within the host cell.

10. The eubacterium according to claim 8 that is an *E. coli*.

11. A method for producing a protein having phosphoserine integrated thereinto, wherein said method comprises providing: (a) a mutant phosphoseryl-tRNA synthetase (SepRS), comprising an amino acid sequence at least 90% identical to SEQ ID NO: 2, wherein the amino acid sequence has at least one of the following modifications: E418N, E420D, E420N, E420Q, E420K, E420R, E418N and E420D, E418N and E420N, E418N and E420Q, E418Q and E420N or E418Q and E420Q, and wherein the binding affinity of said mutant phosphoseryl-tRNA synthetase to a suppressor tRNA is higher than the binding affinity of a wild type phosphoseryl-tRNA synthetase (SepRS) having the amino acid sequence depicted in SEQ. ID NO: 2 to the suppressor tRNA; (b) a suppressor tRNA capable of accepting phosphoserine in the presence of the mutant phosphoseryl-tRNA synthetase; and (c) a gene encoding a desired protein wherein the gene comprises a nonsense mutation or frameshift mutation at a desired position, in the presence of phosphoserine within a cell or a cell extract.

12. A kit for synthesizing a protein having phosphoserine integrated thereinto, wherein the kit comprises (a) a cell extract; (b) a mutant phosphoseryl-tRNA synthetase (SepRS), comprising an amino acid sequence at least 90% identical to SEQ ID NO: 2, wherein the amino acid sequence has at least one of the following modifications: E418N, E420D, E420N, E420Q, E420K, E420R, E418N and E420D, E418N and E420N, E418N and E420Q, E418Q and E420N or E418Q and E420Q, and wherein the binding affinity of said mutant phosphoseryl-tRNA synthetase to a suppressor tRNA is higher than the binding affinity of a wild type phosphoseryl-tRNA synthetase (SepRS) having the amino acid sequence depicted in SEQ ID NO: 2 to the suppressor tRNA; and (c) a suppressor tRNA capable of accepting phosphoserine in the presence of the mutant SepRS.

13. The mutant SepRS according to claim 1, wherein the amino acids corresponding to positions 432, 443, 495 and 520 of SEQ ID NO: 2 are not substituted or deleted.

* * * * *